(12) United States Patent
Wagner et al.

(10) Patent No.: US 10,179,150 B2
(45) Date of Patent: Jan. 15, 2019

(54) DRY PLATELET COMPOSITION

(71) Applicant: LifeCell Corporation, Branchburg, NJ (US)

(72) Inventors: Christopher T. Wagner, Flemington, NJ (US); Jerome Connor, Doylestown, PA (US); John R. Harper, Jamison, PA (US)

(73) Assignee: LifeCell Corporation, Madison, NJ (US)

( * ) Notice: Subject to any disclaimer, the term of this patent is extended or adjusted under 35 U.S.C. 154(b) by 0 days.

(21) Appl. No.: 15/366,768

(22) Filed: Dec. 1, 2016

(65) Prior Publication Data

US 2017/0136064 A1  May 18, 2017

Related U.S. Application Data

(63) Continuation of application No. 12/088,067, filed as application No. PCT/US2006/037741 on Sep. 26, 2006, now abandoned.

(60) Provisional application No. 60/720,851, filed on Sep. 26, 2005.

(51) Int. Cl.
| | |
|---|---|
| *A61K 35/12* | (2015.01) |
| *A61K 35/19* | (2015.01) |
| *A01N 1/02* | (2006.01) |
| *A61K 9/19* | (2006.01) |
| *A61K 31/7076* | (2006.01) |
| *A61K 35/16* | (2015.01) |
| *A61K 45/06* | (2006.01) |
| *A61K 31/4965* | (2006.01) |
| *A61K 31/522* | (2006.01) |
| *A61K 31/5575* | (2006.01) |
| *A61K 31/5578* | (2006.01) |
| *A61K 33/26* | (2006.01) |

(52) U.S. Cl.
CPC ............ *A61K 35/19* (2013.01); *A01N 1/0221* (2013.01); *A01N 1/0226* (2013.01); *A61K 9/19* (2013.01); *A61K 31/4965* (2013.01); *A61K 31/522* (2013.01); *A61K 31/5575* (2013.01); *A61K 31/5578* (2013.01); *A61K 31/7076* (2013.01); *A61K 33/26* (2013.01); *A61K 35/16* (2013.01); *A61K 45/06* (2013.01); *Y02A 50/471* (2018.01)

(58) Field of Classification Search
None
See application file for complete search history.

(56) References Cited

U.S. PATENT DOCUMENTS

| | | |
|---|---|---|
| 4,004,975 A | 1/1977 | Lionetti et al. |
| 4,665,088 A | 5/1987 | Apitz-Castro et al. |
| 4,764,463 A | 8/1988 | Mason et al. |
| 4,774,088 A | 9/1988 | Vora |
| 4,812,310 A | 3/1989 | Sato et al. |
| 4,940,581 A | 7/1990 | Mason et al. |
| 4,983,514 A | 1/1991 | Weithmann et al. |
| 4,994,367 A | 2/1991 | Bode et al. |
| 5,043,261 A | 8/1991 | Goodrich et al. |
| 5,118,512 A | 6/1992 | O'Leary et al. |
| 5,153,004 A | 10/1992 | Goodrich, Jr. et al. |
| 5,162,571 A | 11/1992 | Shiraishi et al. |
| 5,242,792 A | 9/1993 | Rudolph et al. |
| 5,256,559 A | 10/1993 | Maraganore et al. |
| 5,309,723 A | 5/1994 | Thomas et al. |
| 5,364,756 A | 11/1994 | Livesey et al. |
| 5,552,267 A | 9/1996 | Stern et al. |
| 5,580,714 A | 12/1996 | Polovina |
| 5,601,972 A | 2/1997 | Meryman |
| 5,622,867 A | 4/1997 | Livesey et al. |
| 5,629,145 A | 5/1997 | Meryman |
| 5,736,313 A | 4/1998 | Spargo et al. |
| 5,750,039 A | 5/1998 | Brown et al. |
| 5,750,330 A | 5/1998 | Tometsko et al. |
| 5,759,764 A | 6/1998 | Polovina |
| 5,780,295 A | 7/1998 | Livesey et al. |
| 5,800,978 A | 9/1998 | Goodrich, Jr. et al. |
| 5,919,614 A | 7/1999 | Livesey et al. |
| 5,958,670 A | 9/1999 | Goodrich, Jr. et al. |
| 6,007,978 A | 12/1999 | Goodrich, Jr. et al. |
| 6,037,116 A | 3/2000 | Wiggins et al. |
| 6,045,990 A | 4/2000 | Baust et al. |
| 6,127,111 A | 10/2000 | Braun |
| 6,176,089 B1 | 1/2001 | Bouche |
| 6,194,136 B1 | 2/2001 | Livesey et al. |
| 6,221,669 B1 | 4/2001 | Livesey et al. |
| 6,372,423 B1 | 4/2002 | Braun |
| 6,723,497 B2 | 4/2004 | Wolkers et al. |
| 7,879,802 B2 | 2/2011 | Shailubhai et al. |
| 8,034,782 B2 | 10/2011 | Shailubhai |
| 8,486,617 B2 | 7/2013 | Ho et al. |

(Continued)

FOREIGN PATENT DOCUMENTS

| | | |
|---|---|---|
| CA | 2277379 A1 | 5/1999 |
| DE | 40 02 693 A1 | 7/1991 |
| EP | 0 108 588 A2 | 5/1984 |

(Continued)

OTHER PUBLICATIONS

Angelini et al., "Evaluation of four different methods for platelet freezing, in-vitro and in-vivo studies," Vox Sang, 1992, pp. 146-151, vol. 62, No. 3.

(Continued)

*Primary Examiner* — Hope Robinson

(74) *Attorney, Agent, or Firm* — McCarter & English, LLP

(57) ABSTRACT

The invention features a dry platelet composition and methods of making and using the freeze-dried platelet composition.

23 Claims, 10 Drawing Sheets

(56) References Cited

U.S. PATENT DOCUMENTS

| | | |
|---|---|---|
| 2001/0019819 A1 | 9/2001 | Wolkers et al. |
| 2006/0127375 A1 | 6/2006 | Livesey et al. |

FOREIGN PATENT DOCUMENTS

| | | |
|---|---|---|
| EP | 0 291 873 A2 | 11/1988 |
| EP | 0 342 879 A2 | 11/1989 |
| EP | 0 356 257 A2 | 2/1990 |
| EP | 0 367 271 A2 | 5/1990 |
| EP | 0 401 053 A2 | 12/1990 |
| EP | 0 668 013 A2 | 8/1995 |
| JP | 2001 508807 A | 7/2001 |
| JP | 2005 526481 A | 9/2005 |
| JP | 2008 109136 A | 5/2008 |
| WO | WO-90/06128 A1 | 6/1990 |
| WO | WO-91/04659 A1 | 4/1991 |
| WO | WO-91/18504 A1 | 12/1991 |
| WO | WO-93/00806 A1 | 1/1993 |
| WO | WO-93/14191 A1 | 7/1993 |
| WO | WO-93/23997 A1 | 12/1993 |
| WO | WO-94/02015 A1 | 2/1994 |
| WO | WO-96/13158 A2 | 5/1996 |
| WO | WO-96/24018 A1 | 8/1996 |
| WO | WO-98/51147 A1 | 11/1998 |
| WO | WO-99/55346 A1 | 11/1999 |
| WO | WO-99/60849 A1 | 12/1999 |
| WO | WO-03/014305 A2 | 2/2003 |

OTHER PUBLICATIONS

Arnold et al., "Photodegradation of Sodium Nitroprusside: Biologic Activity and Cyanide Release," Anesthesiology, 1984, pp. 254-260, vol. 61, No. 3.
Becker et al., "Effect of Prostaglandin E1 on Harvesting of Plates from Refrigerated Whole Blood," (Abstract), J. Lab. Clin. Med., 1974, pp. 304-309, vol. 83, No. 2.
Bode et al., "Extended Storage of Platelets in an Artificial Medium with the Platelet Activation Inhibitors Prostaglandin E1 and Theorphylline," Vox Sang, 1991, pp. 105-112 vol. 60.
Bode et al., "The Use of Inhibitors of Platelet Activation or Protease Activity in Platelet Concentrates Stored for Transfusion," Blood Cells, 1992, pp. 361-380, vol. 18, No. 3.
Boutron et al., "Reduction of Toxicity for Red Blood Cells in Buffered Solutions Containing High Concentration of 2,3-Butanediol by Trehalose, Sucrose, Sorbitol, or Mannitol," Cryobiology, 1994, pp. 367-373, vol. 31.
Burkhardt et al., JBC, vol. 275, No. 43, pp. 33536-33541 (2000).
Contant et al., "Heparin Inactivation During Blood Storage: Its Prevention by Blood Collection in Citric Acid, Theophylline, Adenoisine, Dipyridamole—C.T.A.D. Mixture," Thrombosis Research, 1983, pp. 365-374, vol. 31, No. 2.
Cook et al., "Cold-Storage of Synthetic Human Epidermis in HypoThermosol," Tissue Engineering, 1995, pp. 361-377, vol. 1 No. 4.
Currie et al., "Inhibition of Cytokine Accumulation and Bacterial Growth During Storage of Platelet Concentrates at 4° C. with Retention of In Vitro Functional Activity," Transfusion, 1997, pp. 18-24, vol. 37, No. 1.
Daszyński et al., "Storage of Erythrocytes at Temperatures −20 to −24° C.," Acta Med. Pol., 1981, pp. 151-160, vol. 22, No. 2.
Fagbemi et al., "Effect of Sodium Nitroprusside and L-arginine Methyl Ester on Rat Hearts Stored at 4° C. for 24 h," Clinical Science, 1998, pp. 557-564, vol. 95.
Fujino et al., "Preharvest Nitroprusside Flush Improves Post-transplantation Lung Function," The Journal of Heart and Lung Transplantation, 1997, vol. 16, No. 10, pp. 1073-1080.
International Search Report and Written Opinion of Application No. PCT/US2006/037741 dated Aug. 27, 2007.
Johnson et al., "Preservation of Platelet Function in Cryopreserved Platelet Concentrates with Prostacyclin," Clin. Lab. Haemat., 1984, pp. 141-144, vol. 6.
Li et al., Cell, vol. 112, pp. 77-86 (2003).
Jung et al., "Hypertonic Cryohemolysis: Ionophore and pH Effects," J. Membrane Biol., 1978, pp. 273-284, vol. 39.
Karrenbrock et al., "Comparison of the Effects of SIN-1, Sodium Nitroprusside and Nitrate Derivatives on the Inhibition of Platelet Aggregation and Activation of Soluble Platelet Guanylate-Cyclase," (PubMed Abstract), Pathol. Biol. (Paris), 1987, pp. 251-254, vol. 35, No. 2.
Kauhanena t al., Arterioscler. Thromb. Vasc. Biol;, pp. 1-8 (2014).
Klebe et al., "Identification of New Cryoprotective Agents for Cultured Mammalian Cells," In Vitro, 1983, pp. 167-170, vol. 19, No. 3.
Kuhne et al., "Flow Cytometric Evaluation of Platelet Activation in Blood Collected into ECTA vs. Diatube-H, a Sodium Citrate Solution Supplemented with Theophylline, Adenosine, and Dipyridamole," American Journal of Hematology, 1995, pp. 40-45, vol. 50.
Mazur, "Freezing of Living Cells: Mechanisms and Implications," The American Physiological Society, 1984, pp. C125-C142, vol. 247.4.
Meryman et al., "Extending the Storage of Red Cells at 4° C.," Transfus. Sci., 1994, pp. 105-115, vol. 15, No. 2.
Moore et al., "Liquid Storage at 4° C. of Previously Frozen Red Cells," Transfusion, 1987, pp. 496-498, vol. 27, No. 6.
Murakami et al., "Potentiating Effect of Adenosine on Other Inhibitors of Platelet Aggregation," Thrombosis et Diathesis Haemorrhagica, 1972, pp. 252-262, vol. 27, No. 2.
Narayanan, "Inhibition of In Vitro Platelet Aggregation and Release and Fibrinolysis," Annals of Clinical Labatory Science, 1989, pp. 260-265, vol. 19, No. 1.
Pellerin-Mendes et al., "In Vitro Study of the Protective Effect of Trehalose and Dextran during Freezing of Human Red Blood Cells in Liquid Nitrogen," Cryobiology, pp. 173-186, 1997, vol. 35.
Pinsky et al., "Cardiac Preservation is Enhanced in a Heterotopic Rat Transplant Model by Supplementing the Nitric Oxide Pathway," The Journal of Clinical Investigation, 1994, pp. 2291-2297, vol. 93.
Rodriguez et al., "Role of Sodium Nitroprusside in the Improvement of Rat Liver Preservation in University of Wisconsin Solution: A Study in the Isolated Perfused Liver Model," (Abstract), J. Surg. Res., 1999, pp. 201-208, vol. 87, No. 2.
Rudowski et al., "Studies of Freezing of Outdated Erythrocyte Concentrates and Their Evaluation After Thawing," Acta Medica Polona, 1978, pp. 337-348, vol. 19, No. 3.
Siffert et al., "Inhibition of Platelet Aggregation by Amiloride," Thrombosis Research, 1986, pp. 235-240, vol. 44.
Smith et al., "Nitroprusside Produces Cyanide Poisoning Via a Reaction with Hemoglobin," The Journal of Pharmacology and Experimental Therapeutics, 1974, pp. 557-563, vol. 191, No. 3.
Stadler et al., "Influence of Cold Storage Altered Red Cell Surface on the Function of Platelets," Journal of Medicine, 1994, pp. 353-361, vol. 25, No. 6.
Teng et al., "Platelet Aggregation Induced by Equinatoxin," Thrombosis Research, 1988, pp. 401-411, vol. 52, No. 5.
Teng et al., "Triwaglerin: A Potent Platelet Aggregation Inducer Purified from Trimeresurus Wagleri Snake Venom," Biochimica et Biophyica Acta., 1989, pp. 258-264, vol. 992, No. 3.
Valeri et al., "A Simple Method for Freezing Human Platelets Using 6% Dimethylsolfoxide and Storage at −80° C.," Blood, 1974, pp. 131-136, vol. 43, No. 1.
Wolkers et al., "Human Platelets Loaded with Trehalose Survive Freeze-Drying," Cryobiology, 2001, pp. 79-87, vol. 42, No. 2.
Wood et al., "Prevention of Monocyte Adhesion and Inflammatory Cytokine Production During Blood Platelet Storage: An In Vitro Model with Implications for Transfusion Practice," Journal of Biomedical Materials Research, 2000, pp. 147-154, vol. 51, No. 2.
Zachara, "The Effect of Persantin on the Phosphate Compounds in Erythrocytes During Blood Conservation," Acta. Haemat, 1972, pp. 164-175, vol. 48.
Zachara et al., "Inorganic Phosphate, Potassium and Sodium in Erythrocytes and in Plasma of Blood Conserved in the Presence of Adenosine and Diphyridamole," Abh. Akad. Wiss. DDR, 1975, pp. 467-471.

(56) References Cited

OTHER PUBLICATIONS

Zhao et al., "Maintenance of Cation Gradients in Cold-Stored Erythrocytes of Guinea Pig and Ground Squirrel: Improvement by Amloride," Cryobiology, 1989, pp. 132-137, vol. 26.
Supplementary European Search Report for European Patent Application No. EP 06 81 5615 dated Aug. 3, 2009.

DRY PLATELET COMPOSITION

This application is a continuation of U.S. application Ser. No. 12/088,067, filed Aug. 19, 2008, now abandoned, which is a national phase filing under 35 U.S.C. § 371 of international application number PCT/US2006/03771, filed Sep. 26, 2006, which claims priority to U.S. Provisional Application No. 60/720,851, filed Sep. 26, 2005. The entire contents of the aforementioned applications are incorporated herein by reference in their entirety.

The research described in this application was supported by contract number W81XWH-05-1-0077 from the Department of Defense. Thus, the government has certain rights in the invention.

TECHNICAL FIELD

The present invention relates to dry platelet compositions, in particular to dry platelet compositions containing one or more inhibitors of platelet activation.

BACKGROUND

Platelets are useful in the treatment of various pathologic conditions such as, for example, wounds, platelet deficiencies (e.g., thrombocytopenia), various genetic or acquired abnormalities, and severe blood loss. However, despite their high demand, the availability of platelets has been limited, at least in part, by their short shelf-life and the inability of current methods to preserve normal platelet function after storage for relatively long periods of time. There is a need therefore to develop platelet compositions that have increased shelf-life.

SUMMARY

The invention is based, in part, on the discovery that platelets dried and rehydrated in the presence of a cryopreservative additive (CPA) containing three inhibitors of platelet activation and cryoprotectants retain all, or a substantial level, of normal function. These findings provide the basis for a dry platelet composition (e.g., a freeze-dried platelet composition) and methods of making a freeze-dried platelet composition. In addition, the invention features methods of treatment.

More specifically, the invention provides a dry platelet composition. The composition includes: a plurality of dry platelets; and one or more inhibitors of platelet activation. The one or more inhibitors of platelet activation can be, for example, effectors of the cyclic adenosine monophosphate (cAMP) second messenger system, sodium channel inhibitors, and/or effectors of the cyclic guanosine 5' monophosphate (cGMP) second messenger system. The one or more inhibitors of platelet activation can include, for example, adenosine, amiloride, and/or sodium nitroprusside. After hydration of the composition, the concentration in the composition: of adenosine can be about 10 µM to about 1 mM; that of amiloride can be about 0.1 mM to about 10 mM; and that of sodium nitroprusside can be about 2.5 µM to about 250 µM. The effectors of the cAMP second messenger system can be, for example, iloprost, prostacyclin, prostaglandin $E_2$, forskolin, cholera toxin, isoproterenol, 8-bromo cyclic adenosine monophosphate, dibutyl cyclic adenosine monophosphate, theophylline, isobutylmethyl xanthine, thyrotropin, and/or auranofin. The sodium channel inhibitors can be, for example, amiloride analogues, bepridil, flecainide, saxitoxin, benzamil, and/or prajnalium. The effectors of the cGMP second messenger system can be, for example, L-arginine, nitrous oxide, SIN-1, SIN-1A, atrial natriuretic factor, vasopressin, oxytocin, and/or glyceril trinitrate. The composition can further induce one or more cryoprotective agents, e.g., dimethylsulfoxide (DMSO), maltodextrin, dextran, hydroxyethyl starch, glucose, polyvinyl pyrrolidone, and/or mannitol. The composition can also further include dry blood plasma. Moreover, the composition can further contain one or more extracellular matrix (ECM) components. The ECM components can be components of particles of particulate acellular tissue matrix, e.g., particles of particulate acellular dermal matrix. The one or more ECM components can be, for example, collagen, elastin, fibronectin, fibrillin, laminin, decorin, fibromodulin, hyaluronic acid, and/or a proteoglycan such as a heparin sulfate, chondroitin sulfate, keratan sulfate, or a dermatan sulfate proteoglycan.

Moreover, hydration of the dry platelet composition can result in a rehydrated platelet composition with substantially the same level of at least one platelet function possessed by a sample of fresh platelets from which the dry platelet composition was derived. The at least one platelet function can be the ability to aggregate or the ability to release one or more growth factors, one or more cytokines, or one or more chemokines. The growth factors or chemokines can be, for example, transforming growth factor-β (TGF-β), members of platelet derived growth factor (PDGF) family, epidermal growth factor (EGF), members of vascular endothelial growth factor (VEGF) family, and/or thymosin β4. Alternatively, the at least one platelet function can be the ability to induce cell (e.g., fibroblast) proliferation. The platelets of the composition can be human platelets.

Any of the platelet compositions described herein can be used as a medicament. In addition, any of the platelet compositions described herein can also be used in the preparation of a pharmaceutical composition (i.e., a medicament) for the treatment of a wound (e.g., a wound that will, or is likely to benefit from, administration of platelets (i.e., any of the platelet compositions described herein)) in or on a subject. The wound can be, for example, an internal wound or a cutaneous wound and can include, but is not limited to, any of the types of wounds described below.

Another aspect of the invention is a method of making a freeze-dried platelet composition. The method includes: providing a sample that contains platelets; making a mixture containing the platelets and one or more inhibitors of platelet activation; and drying the mixture. The one or more inhibitors of platelet activation can be any of those recited above. In the mixture, the concentration of adenosine can be about 10 µM to about 1 mM, the concentration of amiloride can be about 0.1 mM to about 10 mM, and the concentration of sodium nitroprus side can be about 2.5 µM to about 250 µM. The mixture can further include one or more cryoprotective agents such as any of those recited above. The mixture can also further include blood plasma. Drying the mixture can be by, for example, freeze-drying the mixture.

In another embodiment, the invention features a method of treatment. The method includes: identifying a subject that has a wound that will, or is likely to, benefit from administration of platelets; and applying the above-described dry platelet composition to the wound. An alternative method of treatment includes: identifying a subject that has a wound that will, or is likely to, benefit from administration of platelets; rehydrating the above-described dry platelet composition to generate a rehydrated platelet composition; and applying the rehydrated platelet composition to the wound.

In both methods of treatment, the wound can be a cutaneous wound (e.g., a pressure ulcer, a venous stasis ulcer, a diabetic ulcer, an arterial ulcer, an injury wound, a burn wound, a complex soft tissue wound, a failed skin graft or flap, a radiation-induced wound, or a gangrenous wound) or an internal wound (e.g., a wound under or below the skin). Internal wounds can include, but are not limited to, a contusion, a fracture, a fistula, an ulcer, or an injury wound of an internal organ.

The term "dry" as used in reference to platelet compositions, platelets, and other components of the compositions (e.g., blood plasma) means that the platelet compositions, platelets, or other components of the compositions are substantially free of water. "Substantially free of water," as used herein, means containing less than 5 percent (e.g., less than: 4 percent; 3 percent; 1 percent; 0.5 percent; 0.2 percent; 0.1 percent; 0.01 percent; or 0.001 percent) by weight water (including bound and unbound water).

As used herein, a "control wound" is a wound to which a platelet composition of the invention has not been applied. Such a control wound can be in a subject also having a wound to which a platelet composition of the invention has been applied. Alternatively, the control wound can be in another subject. The control wound is preferably of the same type and size and in the same tissue or organ as the wound to which a platelet composition of the invention is applied.

Unless otherwise defined, all technical and scientific terms used herein have the same meaning as commonly understood by one of ordinary skill in the art to which this invention pertains. Preferred methods and materials are describe below, although methods and materials similar or equivalent to those described herein can be used in the practice or testing of the present invention. All publications, patent applications, patents, and other references mentioned herein are incorporated by reference in their entirety. The materials, methods, and examples disclosed herein are illustrative only and not intended to be limiting.

Other features and advantages of the invention, e.g., dry platelet compositions, will be apparent from the following description, from the drawings and from the claims.

DETAILED DESCRIPTION

Figure 1:
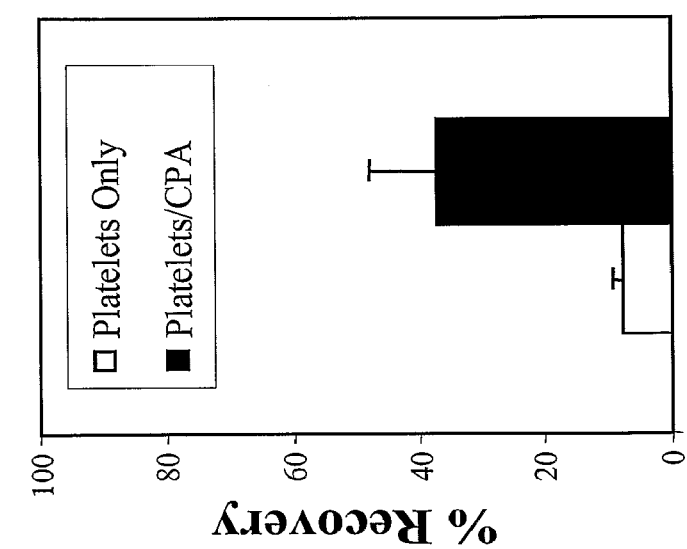
FIG. 1 is a bar graph showing the recovery of the aggregation ability of platelets that had been freeze-dried and rehydrated in the presence or absence of a cryopreservative additive (CPA) solution that contains inhibitors of platelet activation and cryoprotectant agents. The platelet aggregation response was activated by a combination of adenosine diphosphate (10 mM) and collagen (2 µg/ml). The data are presented as the aggregation responses of the freeze-dried and rehydrated platelet samples as percentages of the aggregation response of fresh platelets from the same sample used for making the freeze-dried platelets. The experiment was performed three times using platelet rich plasma (PRP) from a separate donor for each experiment. The data shown are the means obtained from the three experiments and standard deviations are indicated. These means are the means of the averages three replicates in each experimental group.

Platelets constitute an important therapeutic for a variety of platelet diseases or abnormalities involving platelet deficiency and/or defective platelet function (e.g., thrombocytopenias) as well as for the treatment of various wounds. However, the rapid loss of platelet viability and function during storage has greatly complicated management of an effective inventory of platelets in blood banks. In many settings, the limited shelf life of platelets has drastically reduced their usage.

Current guidelines allow platelets to be stored for a maximum of only 5 days at 20° C.-24° C., creating an inventory control problem for hospital and blood banks [Lazarus et al. (1982) Transfusion 22:39-43; Murphy (1985) Seminars in Hematology 22:165-177]. This time restriction was established, at least in part, because of concerns over the potential for microbial contamination during storage of platelets at room temperature. On the other hand, the use of various cryopreservation methods to extend the shelf-life of platelets have not proven very effective. Such methods result in, for example, a loss of normal platelet discoid morphology, a loss of platelet cell number, and a reduction in platelet functional activity [Balduni et al. (1993) Haematologia. 78:101-104; Bock et al. (1995) Transfusion. 35:921-924]. It is desirable therefore to obtain platelets that retain function after storage for prolonged periods of time.

The inventors found that platelets freeze-dried and rehydrated in the presence of a cryopreservative additive (CPA) solution containing inhibitors of platelet activation, retain their functional properties. Platelets freeze-dried and rehydrated with CPA exhibited increased agonist-induced aggregation compared to platelets freeze-dried and rehydrated without CPA and retained their ability to secrete growth factors. In the case of TGF-β (as a representative growth factor), substantially all of the TGF-β-specific antibody detected protein produced by CPA freeze-dried and rehydrated platelets had activity. In addition, CPA freeze-dried and rehydrated platelets secreted factors that induced proliferation in fibroblasts, an important determinant for normal wound closure and remodeling. In a diabetic mouse wound model, delivery to the wound of platelets that had been freeze-dried in the presence of CPA resulted in increased wound healing as assessed by the degree of granulation, wound closure, vascularity and cell proliferation.

These findings provide support for the compositions and methods of the invention, which are described below.

Dry Platelet Compositions

The invention provides a dry platelet composition. The composition is made by drying (e.g., freeze-drying) isolated platelets or preparations or samples (e.g., platelet rich plasma) containing platelets in the presence of one or more (e.g., two or more, three or more, four or more, five or more, six or more, seven or more, eight or more, nine or more, ten or more, or 12 or more) inhibitors of platelet activation. As used herein, "platelet activation" refers to a biological (e.g., thrombin-mediated) or physical (e.g., exposure to cold temperature, e.g., 4° C.) process that lead to a change in shape (discoid to spheroid to amorphous) of the platelet, and/or granule release from the platelet, and or platelet aggregation. An "inhibitor of platelet activation" is an agent that can totally prevent or partially decrease platelet activation.

The preparations or samples containing platelets useful for making the compositions of the invention are preferably free of non-platelet cells. However they can contain small numbers of such cells, e.g., blood cells such as erythrocytes, lymphocytes, granulocytes, monocytes, and/or macrophages. They will preferably contain less than 10% (e.g., less than: 5%; 2%; 1%; 0.1%; 0.01%; 0.001%; or 0.0001%) of any of the non-platelet cell types present in blood from which a relevant platelet preparation or sample was made.

The dry platelet composition of the invention contains a plurality of dry platelets and one or more inhibitors of platelet activation. The one or more inhibitors of platelet activation include one or more effectors (activators or enhancers) of the cyclic adenosine monophosphate (cAMP) second messenger system, one or more inhibitors of sodium channels, and or one or more effectors (activators or enhancers) of the cyclic guanosine monophosphate (cGMP) second messenger system. Other inhibitors of platelet activation include inhibitors of the cyclooxygenase second messenger system, inhibitors of the lipoxygenase pathway, inhibitors of the phospholipase pathway, inhibitors of the calcium cascade, protease and proteinase inhibitors, and membrane modifiers.

Effectors of the cAMP second messenger system include, for example, adenosine, iloprost, prostacyclin, prostaglandin $E_2$, forskolin, cholera toxin, isoproterenol, 8-bromo cyclic adenosine monophosphate, dibutyl cyclic adenosine monophosphate, theophylline, isobutylmethyl xanthine, thyrotropin, and auranofin. Sodium channel inhibitors include, for example, amiloride, amiloride analogues, bepridil, flecainide, saxitoxin, benzamil, and prajnalium. Effectors of the cGMP second messenger system include, for example, sodium nitroprusside, L-arginine, nitrous oxide, SIN-1 (3-morpholinosydnonimine), SIN-1A (N-nitroso-N-morpholinoamino-acetonitrile), atrial natriuretic factor, vasopressin, oxytocin, and glyceril trinitrate. Inhibitors of the cyclooxygenase pathway can be aspirin, dipyridamole, flurbiprofen, ticlopidine, ketoprofen, ibuprofen, indomethacin, sulfinpyrazone, guanabenz, ursolic acid and benzohydroquinone. Inhibitors of the lipoxygenase pathway include aspirin, ticlopidine, ursolic acid, unbelliferone, 5,8,11,14 eicosatetraynoic acid and esculetin. Inhibitors of the phospholipase pathway include quinacrine and mepacrine. Inhibitors of the calcium cascade include protein kinase C effectors, calcium channel blockers, calcium concentration modifiers, calmodulin effectors, calcium ionophores, and ATPase stimulators. Protease and proteinase inhibitors include heparin and aprotinin. Membrane modifiers include amantadine, heparin, ticlopidine, pentoxifylline, and ajoene. Inhibitors of platelet activation are described in greater detail in U.S. Pat. No. 5,919,614, the disclosure of which is incorporated herein by reference in its entirety.

The dry platelet composition of the invention can include adenosine as an effector of the cAMP second messenger system, amiloride as a sodium channel inhibitor, and sodium nitroprusside as an effector of the cGMP second messenger system. The concentration of these inhibitors of platelet activation in the solution in which the platelets are dried, or after rehydration (if they are rehydrated), can be as follows: the concentration of adenosine can be about 10 µM to about 1 mM (e.g., about 100 µM to about 1 mM or about 10 µM to about 0.1 mM); the concentration of amiloride can be about 0.1 mM to about 10 mM (e.g., about 1 mM to about 10 mM or about 0.1 mM to about 1 mM), and the concentration of sodium nitroprusside can be about 2.5 µM to about 250 µM (e.g., about 25 µM to about 250 µM or about 2.5 µM to about 25 µM). For example, in a preferred embodiment, the concentration of adenosine is 0.1 mM, the concentration of amiloride is 0.25 mM, and the concentration of sodium nitroprusside is 50 µM.

The term "about" used in regard to concentrations of inhibitors of platelet activation and cryoprotectants (see below) indicates that the concentration of the agent referred to can vary by up to 20% (e.g., up to: 15%; 10%; 5%; 2.5%; or 1%) of the concentration stated.

In addition to the one or more inhibitors of platelet activation, one or more cryoprotective agents (also referred to herein as cryoprotectants) can be added to platelets before drying. Such cryoprotective agents can be, for example, dimethylsulfoxide (DMSO), maltodextrin, dextran, hydroxyethyl starch, glucose, polyvinyl pyrrolidone, mannitol, and combinations thereof. The DMSO concentration can be from about 0.5% to about 10% (e.g., about 1.0% to about 10%; or about 0.5% to about 1%). In one preferred embodiment, the concentration of DMSO can be 0.5%. Thus, where one or more cryoprotective agents have been added to a platelet preparation before drying, the resulting dry platelet composition will contain the appropriate one or more cryoprotective agents.

Where an inhibitor of platelet activation or a cryoprotective agent that is added to platelets prior to drying is in its pure form a liquid (e.g., DMSO), the dry platelet composition (and its rehydrated form) likely contains less of the inhibitor of platelet activation or the cryoprotective agent than prior to drying.

In addition to inhibitors of platelet activation and cryoprotective agents, the dry platelet compositions of the invention can contain one or more proteins. For example, the compositions can contain dry blood plasma, e.g., dry blood plasma derived from the donor of the platelets. This will inherently be the case where the compositions are made using platelet rich plasma (PRP) as the platelet preparation used for making the composition. In addition, proteins in the composition can be present as dry blood serum. Alternatively, protein can be added to the platelet mixture prior to drying in the form of one or more (e.g., all) isolated blood plasma-derived or blood serum-derived proteins (e.g., albumin or gamma globulins). Blood plasma, blood serum, or protein(s) derived from either can be from the same donor as the platelets (i.e., autologous), one or more donors of the same species, or one or more donors of one more other species. The species from which these protein sources are obtained can be any of those listed below as sources of platelets for the compositions (see below). Moreover, blood or serum proteins can be recombinant proteins.

The dry platelet compositions can also contain one or more extracellular matrix (ECM) components, e.g., any types of collagen (such as, for example, collagens I, II, III, or IV or any of collagens V-XVII), elastin, fibronectin, laminin, decorin, fibrillin, fibromodulin, hyaluronic acid, and/or a proteoglycan such as a heparin sulfate, chondroitin sulfate, keratan sulfate, or a dermatan sulfate proteoglycan. These components can be added to the mixture containing platelets before drying or they can be added after drying. Such ECM components can enhance wound repair by providing a scaffold structure and local binding sites for factors released by administered platelets.

Moreover, when added to platelet mixtures prior to drying by freeze-drying, the ECM components (like the above described protein additives) can substitute for a significant amount of water in the platelet mixture, thereby reducing the amount of ice formed in freezing the platelet mixture and hence reducing ice-mediated damage to the platelets. The ECM components can be obtained from any of the donors described above for blood plasma, blood serum, or proteins derived from either. In addition, ECM that are proteins can be recombinant proteins. The ECM components can be added, for example, in the form of particulate acellular tissue matrix made from any of a variety of collagen-containing tissues, e.g., dermis. Particulate acellular tissue matrices are described in detail in U.S. Pat. No. 6,933,326, U.S. application Ser. No. 10/273,780, and U.S. application Ser. No. 10/959,780, the disclosures of all of which are incorporated herein by reference in their entirety.

A substantial proportion of the platelets of the dry platelet composition regain at least one platelet function (e.g., at least: two; three; or four platelet functions) upon rehydration (in vitro or in vivo). After drying and rehydration, a platelet composition of the invention has at least 10% (e.g., at least 20%, at least 30%, at least 40%, at least 50%, at least 60%, at least 70%, at least 80%, at least 90%, at least 95%, at least 98%, at least 99%, or 100%) of the level of at least one platelet function that a corresponding fresh preparation (not dried and rehydrated, from the same donor, and containing the same number of platelets as the platelet composition of invention) of platelets would have. Moreover, at least 10% (e.g., at least 20%, at least 30%, at least 40%, at least 50%, at least 60%, at least 70%, at least 80%, at least 90%, at least 95%, at least 98%, at least 99%, or 100%) of the platelets of a dry platelet composition of the invention have, upon rehydration, at least one platelet function. Relevant platelet functions include, for example, growth factor, cytokine, and chemokine production upon activation; the ability to stimulate cell (e.g., fibroblast, endothelial cell, or epithelial cell (e.g., keratinocyte)) proliferation upon activation; and the ability to aggregate upon activation. Assays for platelet function are known in the art and include those described in the Examples below. The platelet-produced growth factors, cytokines and chemokines include, without limitation, transforming growth factor-β (TGF-β), members of the platelet derived growth factor family (e.g., PDGF-A, B, C, D, and A/B), epidermal growth factor (EGF), members of the vascular endothelial growth factor (VEGF, VEGF-B, VEGF-C, and VEGF-D), and thymosin-β4. Additional indicia of intact platelet function that can be tested include, without limitation, morphology score (proportion of platelets that are discoid, spheroid, and/or amorphous), extent of shape change (ESC), hypotonic shock response (HSR), extent of shape change (ESC), platelet aggregation (as measured by platelet aggregometry), efficiency of inducing blood coagulation (as measured by thromboelastography (TEG)), and platelet adenosine triphosphate (ATP) levels.

P-selectin expression on the surface of a platelet indicates mat it has degranulated. Degranulation can occur without, for example, aggregation.

Assessment of platelet function in the rehydrated dry platelet compositions can be quantitative, semi-quantitative, or qualitative. Thus it can, for example, be measured as a discrete value or expressed relative to a baseline or to similar measurements in control samples (e.g., fresh platelets). Platelet function can be assessed and expressed using any of a variety of semi-quantitative/qualitative systems known in the art. Thus, platelet viability and/or function can be expressed as, for example, (a) one or more of "excellent", "good", "satisfactory", and/or "poor"; (b) one or more of "very high", "high", "average", "low", and/or "very low"; or (c) one or more of "++++"; "+++", "++", "+", "+/−", and/or "−".

The platelets may be obtained from one or more individuals of any of a variety of mammalian species (e.g., humans, non-human primates (e.g., monkeys, baboons, or chimpanzees), cows, sheep, horses, goats, pigs, dogs, cats, rabbits, guinea pigs, hamsters, gerbils, rats, or mice) but are preferably of the same species as a subject to which they are to be administered. The dry platelet composition can be used in vitro or in vivo. In vitro uses of the dry platelet composition include their use as targets for in vitro screening assays or testing of compounds of interest for, e.g., those with hemostasis-promoting activity, those with hemostasis-inhibiting activity, or those that promote wound healing. The dry platelet composition can be rehydrated (e.g., with a phyiological solution such as normal saline or culture medium) and plated into tissue culture dishes.

The dry platelet compositions can also be used for the in vitro production and subsequent isolation of soluble factors that are expressed by platelets (see above). Such factors are useful as diagnostic tools themselves or can be used as antigens to generate antibodies for diagnostic use. In addition, rehydrated dry platelets of the invention can be used in in vitro drug efficacy or toxicity assays. The dry platelet composition can also be used as "positive controls" in procedures to develop other platelet storage compositions.

Platelets obtained by rehydrating a dry platelet composition of the invention can also be used to support the growth and/or differentiation of non-platelet cells in culture. Such platelets upon activation can promote, for example, the survival and/or growth of fibroblast cells or other cells (e.g., fibroblast, endothelial cell, or epithelial cell (e.g., keratinocyte)) in cell culture. The dry platelet composition can also be used for in vitro and in vivo basic scientific studies of platelet function.

In vivo uses of the dry platelet compositions, or of platelets derived therefrom, include, for example, studies in animal models (e.g., in any of the mammals listed above) or in human subjects. Such studies may be performed, for example, in order to assess the therapeutic and/or prophylactic efficacy of platelets per se or of chemical compounds and biological molecules that modulate (up or down regulate) platelet function. Other uses of the platelet compositions of the invention include methods of treatment (see below).

Methods of isolating platelets are well known in the art. For example, platelets can be prepared by centrifugation of whole blood by either the platelet-rich plasma (PRP) method or the buffy coat method. Moreover, platelets can be collected by various apheresis techniques that are available in the art.

Method of Making Freeze-Dried Platelet Composition

Also embodied by the invention is a method of making a freeze-dried platelet composition. The method includes: (a) providing a preparation or sample of platelets; (b) making a mixture including the platelets and one or more inhibitors of platelet activation; and (c) drying the mixture. The mixture can also optionally contain one or more cryoprotectants, one or more proteins (e.g., blood plasma), and/or ECM components described above.

The preparation or sample of platelets, the inhibitors of platelet activation, and the optional cryprotectants, proteins, and ECM components can be any of those listed above. Drying the mixture can be by any method known in the art, e.g., air drying, drying in atmosphere of, or under a stream of, inert gas (e.g., nitrogen or argon), or freeze-drying.

Freeze-drying methods are well-known in the art (see, for example, "A Guide to Freeze-drying for the Laboratory"-an industry service publication by Labconco, 2004; Franks (1994) Proc. Inst. Refrigeration. 91: 32-39, and U.S. Pat. Nos: 4,619,257; 4,676,070; 4,799,361; 4,865,871; 4,964,280; 5,024,838; 5,044,165; 5,154,007; 6,194,136; 5,336,616; 5,364,756; and 5,780,295, the disclosures of all of which are incorporated herein be reference in their entirety).

Freeze-drying of platelets using one or more inhibitors of platelet activation, and optionally one or more ciyoprotectants, results in minimal, if any, functional damage to the platelets. Suitable freeze-drying equipment is available from commercial sources, e.g., Labconco (Kansas City, Mo.) and VirTis (Gardiner, N.Y.). Freeze-drying a liquid (e.g., water)-containing sample involves freezing the sample and the subsequent removal of liquids (e.g., water) from the frozen sample by a process called sublimation. Freezing can be, for example, in the freeze-drier apparatus or in a −80° C. freezer. The sample is cooled until the liquid in the sample has solidified (as assessed by the visually). Freezing can be at a cooling rate of between, for example, 1° C. and 5° C. per minute and is preferably not by "snap-freezing." Freezing methods are described extensively in the above references cited in regard to freeze-drying. Sublimation occurs when a frozen liquid goes directly to the gaseous state without passing through the liquid phase. Freeze-drying may be accomplished by any of a variety of methods, including, for example, the manifold, batch, or bulk methods.

Method of Treatment

The invention also provides a method of treatment. The method can include identifying a subject that will, or is likely to, benefit from administration of platelets and administering to the subject any of the platelet compositions described above.

The dry platelet compositions can per se be administered to the subject. In this case, rehydration of the platelets occurs in the subject. Alternatively, the platelet compositions can be rehydrated and then administered to the subject. In the latter case, the a composition can optionally, prior to being administered, be subjected to a washing process to remove all or a substantial amount of the one or more inhibitors of platelet activation and, if used in the relevant composition, one or more cryoprotectants. Such washing methods are known in the art and generally involved one or more (e.g., two, three, or four) centrifugation steps. It is particularly desirable to perform such washing steps where inhibitors of platelet activation and/or cryoprotectants used are toxic. In this case, washing is performed until none, or an acceptably low level, of the toxic components remains in the composition.

Rehydration (and optional washing) can be with any physiological solution (e.g., water, normal saline, tissue culture medium, or the physiological solutions described in Examples 1 and 7 below) such that the platelets retain one or more of their functions (see above). The dried platelet compositions can optionally be rehydrated in the pharmaceutically acceptable carrier in which the platelets are to be administered to an appropriate subject (see below). Rehydration can be by rapid immersion of the platelets in the relevant carrier or by gradual (e.g., drop-wise addition of the carrier) to the dry platelets.

The subject that will, or is likely to, benefit from administration of platelets can have a wound. The wound can be one that will, or is likely to, benefit from being treated with platelets. The wound can be a cutaneous wound that can be, or can be a result of, a pressure ulcer, a venous stasis ulcer, a diabetic ulcer, an arterial ulcer, an injury wound, a burn wound, a complex soft tissue wound, a failed skin graft or flap, radiation-induced tissue damage, and a gangrenous wound. The wound can also be an internal wound of any internal organ or tissue, e.g., gastrointestinal tissue, pulmonary (e.g., lung or bronchial) tissue, heart tissue, connective tissue (e.g., tendon, ligament, and cartilage), bone tissue, neural (central and peripheral nerve system) tissue, and vascular (vein and artery) tissue. Internal wounds of interest include, without limitation, contusions, fractures, fistulas, ulcers, or internal organ injuries (e.g., injury of the intestine, spleen, liver, lungs, or heart). The wound can be caused by a trauma, including, e.g., a compound fracture, a gunshot wound, or an abrasion from an accident.

The dry (or rehydrated) platelet composition can be delivered to a wound immediately after it occurs or at any stage of its natural healing process. Preferably, the platelet composition will be delivered to the wound immediately, or soon after, the wound is detected, or formed, in the subject. The wound that is to be treated with the platelet composition can have varying appearance, size, depth (i.e., stage), and color, and can include, for example, the presence of hematomas, seromas, wound exudate, necrotic tissue, and eschar.

The dry (or rehydrated) platelet composition can be applied topically, i.e., directly to the wound. It can be applied to the wound by any suitable means, such as by sprinkling or spraying the platelets onto the wound, packing the platelets into the wound, or by means of a surgical aid as discussed below. Sprayable aerosol preparations can include the platelet composition in combination with a solid or liquid inert carrier material and can be packaged in a squeeze bottle or in admixture with a pressurized volatile, normally gaseous propellant, e.g., a freon.

Dry platelets may be applied to the wound by means of a surgical aid, such as, for example, a wound dressing or bandage, a suture, a fabric, or a prosthetic device. Such aids can include, for example, a solid physiologically acceptable substrate material and platelets on or in (e.g., applied as a coating on or impregnated in) the substrate material. Typically, such surgical aids are provided in a sterile form packaged in a sterile container. The surgical aid substrate material may be coated with the platelets, e.g., by sprinkling dry platelets onto the material or by impregnating the surgical aid substrate with, or applying to its surface, a liquid suspension of fresh platelets containing the one or more inhibitors of platelet activation (and optionally one or more cryoprotectants) and drying (e.g., freeze-drying) the surgical aid/platelet mixture so that the platelets adhere to the surgical aid substrate. Alternatively, dry platelets can be adhered to the surgical aid substrate with a suitable adhesive material, or simply sprinkled onto the surgical aid prior to application of the surgical aid to the subject.

The surgical aid can be of any suitable shape and size and be made of any suitable solid material, hydrophobic or hydrophilic, which is physiologically acceptable. Sutures, for example, may be monofilament or braided, can be biodegradable, and can be made of materials such as, for example, nylon silk, polyester, or cotton. Prosthetic devices, for example, include woven or extruded tubular structures, having use in the repair of arteries, veins, ducts; fabrics useful surgically in hernia repair and in supporting damaged liver, kidney, or other internal organs; pins, screws, and reinforcing plates; heart valves, artificial tendons, or cartilage material. Bandages can be made of any suitable substrate material, such as cotton or other fabric suitable for application to or over a wound, can optionally include a backing material, and can optionally include one or more adhesive regions on the face surface thereof for securing the bandage over the wound.

The platelet compositions of the invention are administered to subjects in pharmaceutically acceptable formulations that include a pharmaceutically acceptable carrier. A pharmaceutically acceptable carrier e.g., normal saline, excipient, or stabilizer, can be added to the cells before they are administered to a subject. The phrase "pharmaceutically acceptable" refers to molecular entities and compositions that, at the concentration used, are not deleterious to cells, are physiologically tolerable, and typically do not produce an allergic or similar untoward reaction, such as gastric upset, dizziness and the like, when administered to a human.

Suitable formulations include, but are not limited to, solutions, suspensions, emulsions, creams, ointments, powders, liniments, salves, and aerosols, which are, if desired, sterilized or mixed with auxiliary agents, e.g., preservatives, stabilizers, wetting agents, antiseptic agents, antimicrobial agents (e.g., hydrogen peroxide, Betadine, or acetic acid), or buffers or salts for influencing osmotic pressure. A wide variety of pharmaceutically acceptable carriers, excipients or stabilizers are known in the art [Remington's Pharmaceutical Sciences, 16th Edition, Osol, A. Ed. 1980]. Pharmaceutically acceptable carriers, excipients, or stabilizers include: buffers, such as phosphate, citrate, and other nontoxic organic acid buffers; antioxidants such ascorbic acid; low molecular weight (less than 10 residues) polypeptides; proteins such as serum albumin, gelatin or immunoglobulins; hydrophilic polymers such polyvinylpyrrolidone; amino acids such as glycine, glutamine, asparagine, arginine, or lysine; monosaccharides, disaccharides, and other carbohydrates including glucose, mannose, or dextrans; chelating agents such as EDTA; sugar alcohols such as mannitol, or sorbitol; salt-forming counterions such as sodium; and/or nonionic surfactants such as Tween, Pluronics, or PEG.

The dosage of the platelet composition required depends on the nature of the formulation, the nature of the wound or the type and severity of the wound that is to be treated, the subject's size, weight, surface area, age, and sex, other therapeutic agents being administered, and the judgment of the attending physician. Wide variations in the needed dosage are to be expected in view of differing efficiencies of various routes of administration. Platelet compositions can be applied to wounds such that about 1 ml of rehydrated composition is applied for each about 1 $cm^3$ of wound. Variations in these dosage levels can be adjusted using standard empirical routines for optimization as is well understood in the art.

The platelet compositions can be administered to a subject once or multiple times. Thus, the compositions can be administered one, two, three, four, five, six, seven, eight, nine, ten, 11, 12, 13, 14, 15, 17, 20, 25, 30, 35, 40, 45, 50, 60, 70, 80, 100, 150, 200, 250, 300, 350, 400, 450, 500, 700, 1000, or more times. Where a plurality of administrations is made, the administrations can separated by any appropriate time period, e.g., 30 seconds, one minute, two minutes, three minutes, four minutes, five minutes, 10 minutes, 20 minutes, 30 minutes, 45 minutes, 1 hour, two hours, three hours, four hours, five hours, eight hours, 12 hours, 18 hours, 24 hours, two days, three days, four days, a week, two weeks, three weeks, a month, two months, three months, four months, five months, six months, eight months, ten months, a year, 18 months, two years, three years, four years, or five years.

The platelets can be obtained from the individual to whom the platelet composition is to be administered (the recipient), i.e., the platelets can be autologous. Alternatively, they can be from one or more individuals of the same species as the recipient, e.g., the platelet composition can be made from a pool of platelets samples prepared from a plurality (e.g., 2, 3, 4, 5, 6, 7, 8, 9, 10, 11, 12, 15, 20, 25, 30, 35, 40, 50, 60, 70, 80, 90, 100 or more) of subjects, e.g., human volunteers. A recipient can also be of a species other than the donor. In addition, platelets can be isolated from the blood of adult, infant, or fetal blood of one or more individuals. Recipients and donors of platelets can be of any other species listed above.

As used herein, "therapeutic" or "therapy" means a complete abolishment of the symptoms of a pathological condition (e.g., a wound) or a decrease in the severity of the symptoms of the pathological condition. "Prevention" means that symptoms of the pathological condition are essentially absent. As used herein, "prophylaxis" means complete prevention of the symptoms of a pathological condition, a delay in onset of the symptoms of a pathological condition, or a lessening in the severity of subsequently developed pathological condition symptoms.

The following examples are meant to illustrate, not limit, the invention.

EXAMPLES

Example 1

Preparation of Platelet Compositions Used in Examples 1-6

Collection of Human Platelet-rich Plasma (PRP)

PRP samples in the form of random donor units (RDU) of human platelets were purchased from an American Association of Blood Banks (AABB) accredited blood bank, stored with agitation at room temperature, and used within 5 days of donation. All required donor-screening and release-testing were performed by the blood bank in accordance with AABB requirements [MEB Technical Manual 14$^{th}$ ed. Bethesda, Md.: American Association of Blood Banks (2002)].

Freeze-drying of PRP

An aliquot of PRP was mixed with a cryopreservative additive (CPA) solution consisting of the metabolic inhibitors amiloride, adenosine, and sodium nitroprusside and the cryoprotectants polyvinyl pyrrolidone (PVP), mannitol, and dimethylsulfoxide (DMSO). These compounds were all diluted in isotonic buffer (buffer B described in Example 7). A separate control PRP aliquot was mixed with isotonic buffer only. The final concentration of platelets in the treated and control PRP samples was $9 \times 10^5$ cells/µl and the final concentrations of the metabolic inhibitors and cryoprotectants were as follows: amiloride (0.25 mM), adenosine (0.1 mM), sodium nitroprusside (50 µM), polyvinyl pyrrolidone (4% w/v), mannitol (50 mM), and dimethylsulfoxide (0.5% v/v).

Both platelet samples were frozen at a cooling rates of between 1° C. and 5° C. per minute and then freeze-dried under standard conditions. After freeze-drying, the PRP samples were stored for less than 5 days at −80° C. and then rehydrated by rapid whole volume addition with buffer B to the volume prior to freeze-drying.

Example 2

Platelets Freeze-Dried and Rehydrated in the Presence of CPA Exhibit Increased Platelet Aggregation To determine whether platelets freeze-dried and rehydrated with CPA are capable of mediating functions important for hemostasis, the aggregation potential of samples freeze-dried and rehydrated with and without CPA was studied in the presence of adenosine disphosphate (10 µM) and type I equine collagen (2 µg/ml; Chrono-Log Corp, Havertown, Pa.). For these studies, in contrast to other experiments described below, the CPA-treated and control freeze-dried were washed once with buffer B. The concentration of platelets in both samples was then adjusted to $3 \times 10^5$ platelets/µl with buffer B and both sample were incubated at 37° C. for one hour after which the adenosine and collagen were added at the indicated concentrations. Aggregation was measured with an optical aggregometer while maintaining the sample temperature at 37° C. The data are presented as aggregation response of freeze-dried and rehydrated platelets expressed as a percentage of the aggregation response of fresh platelets (of the sample PRP sample used for making the freeze-dried samples).

Platelets freeze-dried and rehydrated in the presence of CPA showed an increase in aggregation capacity relative to control freeze-dried platelets (FIG. 1).

Example 3

Platelet Growth Factor Release Assay

In an initial validation of an assay to measure growth factor release from thrombin-activated platelets, fresh platelet suspensions (that had not been frozen or freeze-dried and rehydrated) were tested. The fresh platelet PRP samples were diluted to a concentration of $3 \times 10^5$ cells/µl with buffer B and activated with thrombin (1 unit/ml) for 5 minutes at room temperature. The resulting platelet clot was centrifuged and the supernatant was separated from the pelleted clot. The concentrations in the supernatant of four growth factors were measured by enzyme-linked immunosorbent assays (ELISA) using a commercially available kit (R & D Systems, Minneapolis, Minn.) according to the manufacturer's directions. The growth factors were transforming growth factor-beta (TGF-β), platelet derived growth factor (PDGF A/B), epidermal derived growth factor (EGF), and vascular endothelial growth factor (VEGF).

The data are presented as the amounts of growth factor released in the thrombin-activated supernatant expressed as percentages of the amount of growth factor released by sonication of a corresponding sample of the same platelets (Table 1). The experiment was performed three times using PRP from a separate donor for each experiment. The data are the means obtained from the three experiments and standard deviations are indicated. These means are the means of the averages of three replicates in each experimental group.

As shown in Table 1, for all four growth factors, approximately 50% of sonication-releasable growth factor was released from fresh platelets by thrombin activation.

TABLE 1

Growth Factor Release from Fresh Human Platelets

| Growth Factor | Release |
|---|---|
| TGF-β | 60.4% ± 18.8% |
| PDGF | 55.7% ± 16.0% |
| EGF | 50.8% ± 19.0% |
| VEGF | 47.0% ± 7.8% |

Example 4

Growth Factor Release of CPA-containing Freeze-dried and Rehydrated Platelets

The effect of freeze-drying and rehydration of platelets in the presence and absence of CPA on platelet growth factor release was determined. Data obtained for TGF-β as a representative growth factor are shown in Table 2. ELISA assays (as in Example 3) were performed on the following samples:
(a) a supernatant obtained by centrifugation of the PRP sample used for freeze-drying ("Fresh" "Plasma").
(b) the same PRP sample after sonication ("Fresh" "Sonicate"); this measurement gave the total TGF-B releasable from platelets in the PRP sample plus the TGF-B in the plasma of the PRP sample.
(c) supernatants obtained by centrifugation of samples of freeze-dried and rehydrated (in the presence and absence of CPA) PRP ("F/D/R" "Plasma").
(d) freeze-dried and rehydrated (in the presence and absence of CPA) PRP samples after sonication ("F/D/R" "Sonicate").
(e) supernatants obtained by centrifugation of thrombin-treated (as in Example 3), freeze-dried and rehydrated (in the presence and absence of CPA) PRP; the amounts detected in these supernatants minus the amounts detected in (c) were expressed as a fraction (percentage) of the amounts detected in (d) minus the amounts detected in (c) ("Release").

CPA components were not washed out of the samples before testing. The experiment was performed three times using PRP from a separate donor for each experiment. The data are the means obtained from the three experiments and standard deviations are indicated. These means are the means of the averages of three replicates in each experimental group.

TABLE 2

Release of TGF-β by Freeze-Dried and Rehydrated Platelets (with or without CPA)

| Condition | | TGF-β (ng/ml) PRP | |
|---|---|---|---|
| | | PRP without | PRP with |

TABLE 2-continued

Release of TGF-β by Freeze-Dried and Rehydrated Platelets (with or without CPA)

| Condition | | TGF-β (ng/ml) PRP | |
|---|---|---|---|
| | | CPA | CPA |
| Plasma | | 33.6 ± 5.5 | 28.2 ± 2.3 |
| F/D/R Sonicate | | 57.5 ± 12.0 | 57.1 ± 9.1 |
| Release | | 16.9% | 40.4% |

F/D/R; freeze-dried an drehydrated

Freeze-drying and/or rehydration of both CPA-treated and untreated platelets resulted in a significant level of spontaneous leakage of TGF-β compared to fresh platelet suspensions (Table 2). However, this spontaneous leakage was somewhat lower in the platelets freeze-dried in the presence than in the absence of CPA. Most importantly, platelets that had been freeze-dried and rehydrated in the presence of CPA have a substantially higher ability to release TGF-β than platelets freeze-dried and rehydrated without CPA. Similar results were observed for the other three growth factors listed above.

Example 5

TGF-β Produced by Platelets Freeze-dried and Rehydrated in the Presence of CPA is Active The levels of active TGF-β, as measured by a cellular assay (see below), and the levels of total TGF-β protein, as measured by ELISA, in supernatants from sonicated fresh PRP and sonicated PRP freeze-dried and rehydrated (F/D/R) with CPA were compared (Table 3). These supernatants were the same as some of those shown in Table 2. The cell culture assay used to measure TGF-β activity was that described in Abe et al. [(1994) Anal. Biochem. 216 (2):276-284], the disclosure of which is incorporated herein by reference in its entirety. The experiment was performed three times using PRP from a separate donor for each experiment. The data are the means obtained from the three experiments and standard deviations are indicated. These means are the means of the averages of three replicates in each experiment.

Essentially all the TGF-β released from sonicated fresh platelets and sonicated platelets freeze-dried and rehydrated with CPA was active (Table 3). The same results were obtained with sonicated platelets freeze-dried and rehydrated without CPA.

TABLE 3

Measurements of TGF-β Activity in Human Platelets

| Condition | Total TGF-β protein (ns/ml) | TGF-β Activity (ns/ml) | Percent of TGF-β protein that is active |
|---|---|---|---|
| Fresh Sonicate | 65.3 ± 11.2 | 57.1 ± 2.9 | 87.4% |
| F/D/R (CPA) Sonicate | 57.1 ± 9.1 | 57.9 ± 3.0 | 100% |

| Fresh | Plasma | 18.1 ± 0.7 |
| | Sonicate | 65.3 ± 11.2 |

Example 6

Cellular Proliferation Assay

Assay Design and Validation

Figure 2A:
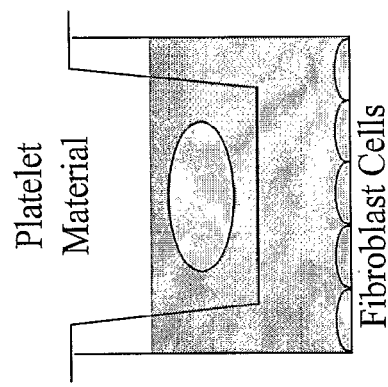
FIG. 2A is a diagrammatic representation of the "Transwell®" cell culture system used to measure proliferation of fibroblasts in response to soluble factors released by platelets. Fibroblast cells were seeded onto the bottom surfaces of the wells of 24-well tissue culture plates and test platelet materials were added to Transwell® chambers having floors consisting of semi-permeable membranes that permit the diffusion of soluble factors (but not whole platelets or insoluble platelet material) from the Transwell® chambers into the culture well where they come in contact with the fibroblasts.

To test for cell proliferation-inducing activity in soluble factors released by thrombin-activated platelets, an in vitro "Transwell®" cell culture system was used. FIG. 2A is a diagrammatic representation of this "Transwell®" cell culture system. Swiss Albino mouse 3T3 fibroblast cells were plated at a density of 10,000 cells per well onto the bottom surfaces of culture wells of 24-well tissue culture plates in Growth Medium (GM; Dulbecco's Modified Eagle's Medium supplemented with 4mM glutamine, 405 g/L glucose, 1.5 g/L sodium bicarbonate, and 10% calf serum (Invitrogen, Carlsbad, Calif.) and cultured for 16 hours at 37° C. in a humidified atmosphere of 5% $CO_2$. In cultures to which activated or sonicated platelets (and corresponding control cultures) were added (see below), the GM was replaced with serum reduced medium (SRM; same as GM but supplemented with 0.5% rather than 10% calf serum). Sonicated or thrombin-activated (1 unit/ml for 5 minutes at 37° C.) platelets (in 75 µl of $1.2 \times 10^6$ platelets per µl) and SRM (225 µl of $1.2 \times 10^6$ platelets per µl) were added to Transwell® chambers having bottoms consisting of semi-permeable membranes (having 8 µm pores) and the chambers were placed above the cells in appropriate culture wells such that the bottoms of the chambers were submerged in culture media in the culture wells (see FIG. 2A). This culture system permitted culture media and soluble factors (but not whole platelets or insoluble platelet material) to diffuse through the semi-permeable membranes and contact the fibroblasts on the culture well bottoms. "Positive control" cultures contained GM and no platelet material. The cultures were incubated for the indicated periods of time after which proliferation was determined by an MTS [3-(4,5-dimethyl-thiazol-2-yl)-5-(3-carboxymethoxyphenyl)-2-(4-sulfophenyl)-2H-tetrazolium, inner salt] metabolic conversion assay. This involved: (a) removal of the Transwell® chambers and culture medium from culture wells; (b) addition to the wells of 0.5 ml fresh SRM and 100 ul of CellTiter96® Aqueous One solution (Promega Corporation, Madison, Wis.); and (c) a further incubation (under the same conditions described above) for 3 hours. Supernatants (100 µl) from each culture were transferred to the wells of 96-well microliter plates and the $OD_{540}$ (as a measure of relative cell proliferation) of each was measured using a microliter plate reader (BioRad, Hercules, Calif.).

Figure 2B:
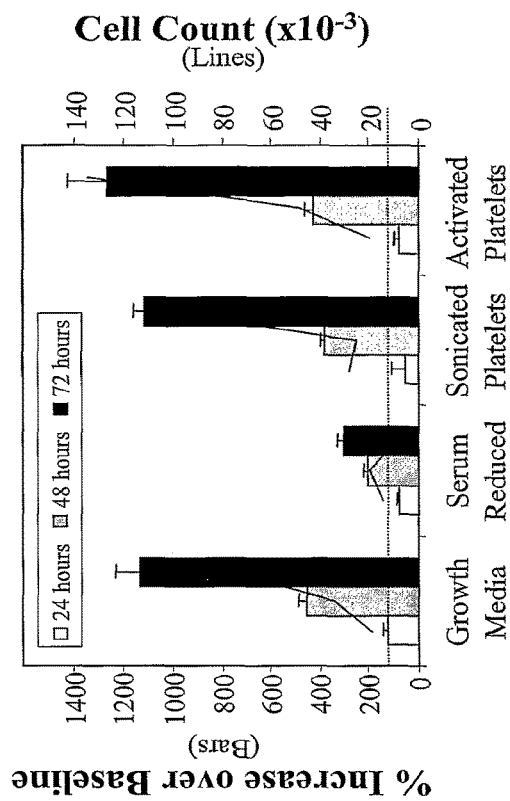
FIG. 2B is a bar and line graph showing the induction of proliferation in fibroblasts at 24, 48, and 72 hours of exposure to growth media alone, serum reduced medium alone, or serum reduced medium and soluble factors released from sonicated platelets or platelets that had been activated with 1 unit/ml of thrombin in the Transwell® culture system described in FIG. 2A. The graph bars represent percent increase in the amount of colored product produced by metabolic conversion of the substrate MTS [3-(4,5-dimethylthiazol-2-yl)-5-(3-carboxymethoxyphenyl)-2-(4-sulfophenyl)-2H-tetrazolium, inner salt] (as an indication of relative cell number) over baseline (left y-axis) and the graph lines represent actual cell counts (right y-axis). The horizontal dashed line indicates the number of cells at the time of initial exposure of the fibroblasts to platelet material (i.e., time 0). The experiment was performed three times using PRP from a separate donor for each experiment. The data are the means obtained from the three experiments and standard deviations are indicated. These means are the means of the averages of three replicates in each experimental group.

Measurements of cellular proliferation were recorded in separate culture wells every 24 hours, for a total of 72 hours after introduction of the Transwell® chambers containing the test platelet materials into culture vessel wells, (FIG. 2B). In FIG. 2B, the graph vertical bars represent percent increase in MTS levels over baseline levels (as measured at time 0, i.e., the time at which the Transwell® chambers containing platelet materials were added to the cultures) (left y-axis) and the graph lines represent actual cell counts (right y-axis). The horizontal dashed line indicates number of cells (right y-axis) at time 0. Sonicated platelets and platelets activated with 1 unit/ml thrombin increased fibroblast proliferation in a time-dependent fashion (compared to cultures containing SRM only).

Figure 2C:
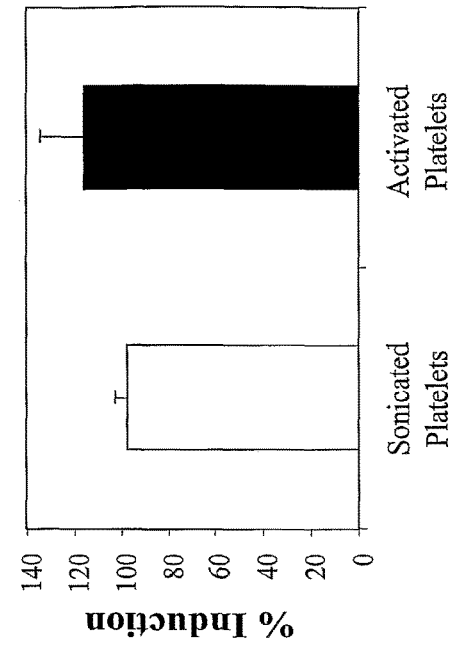
FIG. 2C is a bar graph showing the percent induction of fibroblast proliferation after 72 hours of exposure to soluble factors released from sonicated and activated platelets. The data were obtained from the observations at the 72 hour time point of the experiment shown in FIG. 2B. The experiment was performed three times using PRP from a separate donor for each experiment. The data are the means obtained from the three experiments and standard deviations are indicated. These means are the means of the averages of three replicates in each experimental group.

The cell proliferation levels obtained at 72 hours with sonicated and thrombin-activated platelets minus the minimal level of cell proliferation (observed in cultures containing SRM only) were expressed as percentages of the maximal level of cell proliferation (observed in cultures containing GM only) minus the minimal level of cell proliferation (observed in cultures containing SRM only). The values obtained are referred to as "% induction" (FIG. 2C).

Figure 3:
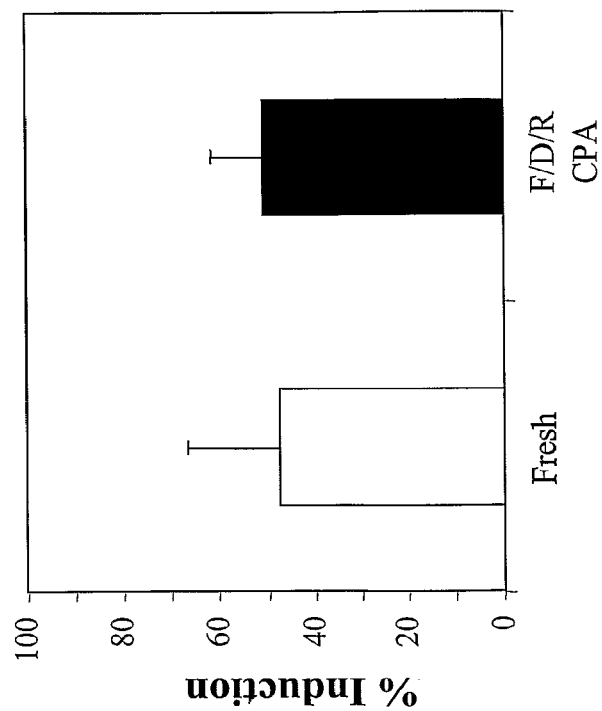
FIG. 3 is a bar graph showing the percent induction of fibroblast proliferation (calculated from data obtained using the Transwell® cell culture system shown in FIG. 2A) in response to fresh platelets and platelets freeze-dried and rehydrated in the presence of CPA (F/D/R CPA). The experiment was performed three times using PRP from a separate donor for each experiment. The data are the means obtained from the three experiments and standard deviations are indicated. These means are the means of the averages of three replicates in each experimental group.

Soluble Factors Produced by Platelets Freeze-dried and Rehydrated in the Presence of CPA Retain the Ability to Induce Cellular Proliferation The above-described in vitro cellular proliferation assay was used to determine the effect of freeze-drying and rehydration in the presence of CPA on the ability of platelets to induce cell proliferation. Platelets were mixed with CPA solution, freeze-dried, and resuspended in buffer B as described in Example 1. The same controls described for the experiment shown in FIG. 2 were performed and the data were calculated as described for FIG. 2C. Platelet preparations which had been freeze-dried and rehydrated with CPA exhibited approximately the same % induction of proliferation as fresh platelets after activation with thrombin (FIG. 3).

Figure 4:
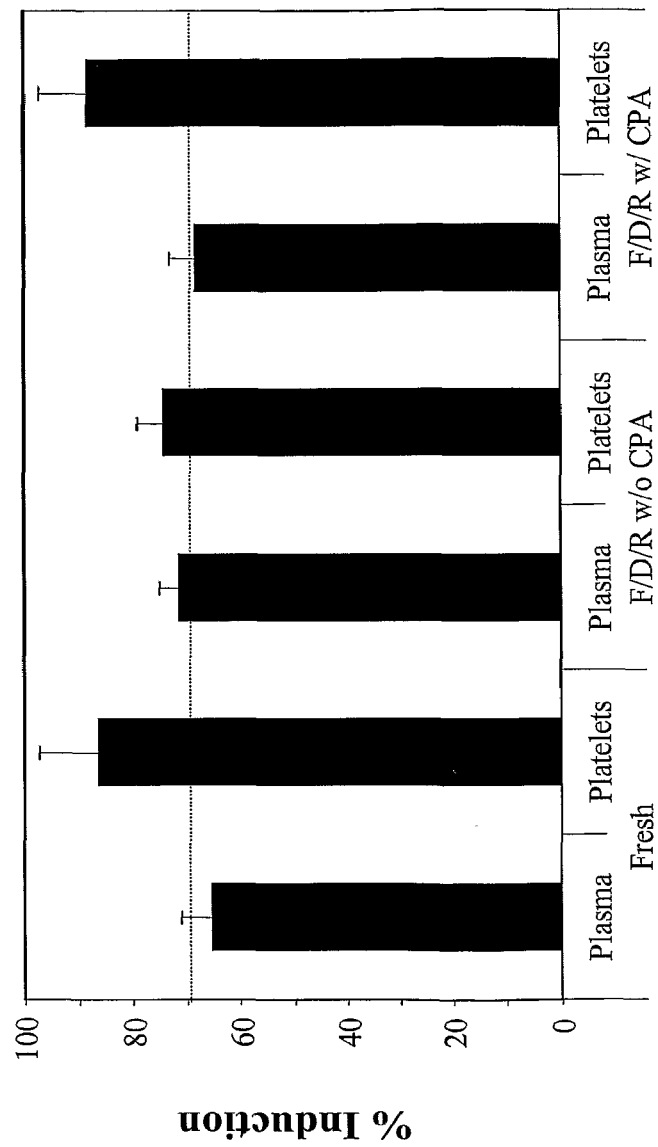
FIG. 4 is a bar graph showing the percent induction of fibroblast proliferation (calculated from data obtained using the Transwell® cell culture system shown in FIG. 2A) after treatment with fresh platelets, platelets freeze-dried and rehydrated (F/D/R) in the presence of CPA (w/CPA) or the absence of CPA (w/o CPA), or plasma obtained by centrifugation of the platelet rich plasma (PRP) that was the source of the platelets used to make the freeze-dried platelet preparations or by centrifugation of the two rehydrated freeze-dried samples. The dotted line shows the average percent induction of fibroblast proliferation by all three plasma samples. The experiment was performed three times using PRP from a separate donor for each experiment. The data are the means obtained from the three experiments and standard deviations are indicated. These means are the means of the averages of three replicates in each experimental group.

Supernatants from centrifuged fresh platelets PRP, platelets freeze-dried and rehydrated in the absence of CPA, and platelets freeze-dried and rehydrated in the presence of CPA ("Plasma" data in FIG. 4) and supernatants of from the same three samples after thrombin activation were tested in an assay essentially the same as that in the experiment depicted in FIG. 2 ("Platelets" data in FIG. 4). Platelets freeze-dried and rehydrated with CPA, but not those freeze-dried and rehydrated without CPA, retained the ability of fresh platelets to induce cell proliferation (FIG. 4). The dotted line in FIG. 4 shows the average ability of plasma samples to induce fibroblast proliferation.

In addition, a PRP sample freeze-dried in the presence of CPA was divided into several aliquots that were stored at −80° C. for various periods of time up to 24 weeks. The samples were rehydrated at the relevant time points and tested for their ability to induce fibroblast proliferation in the Transwell® culture system described above. All samples demonstrated the same ability to induce fibroblast proliferation as a control sample that was tested without storage.

Figure 5:
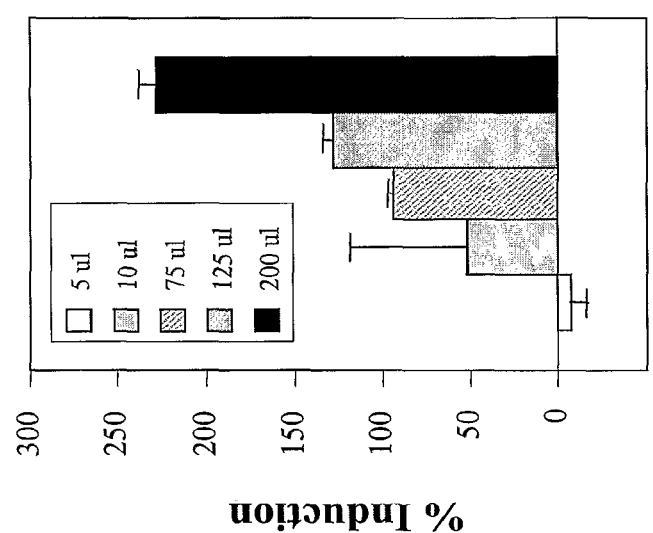
FIG. 5 is a bar graph showing the ability of various amounts of platelets (freeze-dried and rehydrated in the presence of CPA) to induce fibroblast proliferation as assessed using the Transwell® cell culture system shown in FIG. 2A. The legend indicates the relative amounts of platelets added to the Transwell® chambers of the culture system. The experiment was performed three times using PRP from a separate donor for each experiment. The data are the means obtained from the three experiments and standard deviations are indicated. These means are means of three replicates in each experiment.

Ability of Freeze-Dried Platelets to Induce Cellular Proliferation is Dose-Dependent Platelets were freeze-dried and rehydrated in the presence of CPA and thrombin activated as described above. Various volumes of the sample (at the same platelet concentration) were tested in the Transwell® fibroblast proliferation assay system described above by addition of the rehydrated platelet samples to the Transwell® chambers (FIG. 5). Measurements were made after 72 hours of culturing in the presence of the activated platelets. The ability of the thrombin activated freeze-dried platelets to induce proliferation of fibroblast cells was dose-dependent on the amount of rehydrated platelets added to the assay system.

Example 7

CPA-Treated Freeze-Dried Platelets Increase Wound Healing in a Diabetic Mouse Wound Model Materials and Methods
Preparation of Platelet Therapeutics Single donor units (SDU) of human platelets were purchased from an American Association of Blood Banks (AABB) accredited blood bank, stored with agitation at room temperature, and used within 5 days of donation. All required donor-screening and release-testing were performed by the blood bank in accordance with AABB requirements [MEB Technical Manual 14$^{th}$ ed. Bethesda, Md.: American Association of Blood Banks (2002)]. Each SDU was divided into three aliquots to prepare three unique platelet-based therapeutic materials. The first aliquot was adjusted to $1.2 \times 10^6$ platelets/µl with a CPA-containing solution using as a solvent a physiologic buffer [buffer B; 136 mM NaCl, 11.9 mM $NaHCO_3$, 5.6 mM glucose, 5 mM HEPES, 2.7 mM KCl, 2.0 mM $MgCl_2$, 0.42 mM $NaH_2PO_4$; pH 7.4] and freeze-dried, thereby creating a CPA stably preserved freeze-dried platelet rich plasma (FDP-CPA). The second aliquot was adjusted to $1.2 \times 10^6$ platelets/µl using Buffer B and freeze-dried to create a freeze-dried platelet rich plasma (FDP) sample. The third aliquot was adjusted to $1.2 \times 10^6$ platelets/µl using buffer B, sonicated for 10 seconds to disrupt cellular structure and release intracellular constituents, and frozen at $-80°$ C. creating a fresh frozen platelet (FFP) sample. Addition of the CPA protectant solution yielded a final treatment composition of 250 µM amilioride, 100 µM adenosine, 50 µ,M sodium nitroprusside, 1% (v/v) dimethyl sulfoxide, 4% (w/w) polyvinyl pyrrolidone (Plasdone™ C-15, International Specialty Products, Wayne, N.J.), and 50 mM mannitol. All manipulations of the platelet material were done using standard aseptic technique and all solutions were filter sterilized using filters having 0.2 µm diameter pores (Millipore, Billerica, Mass.). Platelet concentrations were verified using a CellDyn® 1700 hematology analyzer (Abbott Laboratories, Abbott Park, Ill.). The dried platelet products were packed under dry nitrogen in heat-sealed foil pouches and stored at $-80°$ C. until used.

Wound Model & Treatment Procedure

Homozygous genetically diabetic 8-12 week-old, Lep/r-db/db male mice (strain C57BL/KsJ-Lepr$^{db}$) were used under an approved animal protocol in an AAALAC accredited facility. The day before surgery, hair was clipped and depilated (Nair®; Church & Dwight Co., Princeton, N.J.). On the day of the surgery (post operative day 0; POD 0), animals were weighed and anesthetized with 60 mg/kg Nembutal® (pentobarbital sodium). A dorsal 1.0 $cm^2$ area of skin and panniculus carnosus was excised and the wounds were photographed. Simultaneously, the following platelet-based treatments were prepared: the FFP samples were thawed, while the freeze-dried samples, FDP and FDP-CPA, were rehydrated with sterile $dH_2O$ to their original volume. The three different platelet treatments, with equivalent platelet concentrations, based on pre-processing determinations, were divided into 250 µl aliquots. Each aliquot was treated with 1 U/ml thrombin (Chronolog Corporation, Havertown, Pa.) just prior to application and allowed to clot in situ, thereby facilitating persistence of the platelet material in the wound. Fifteen wounds in each platelet experimental group (NT (not treated), FFP, FDP and FDP-CPA) were included. All wounds were covered with a semi-occlusive polyurethane dressing (Tegaderm™, 3M, St. Paul, Minn.). On post operative day 9 (POD 9), the animals were euthanized and the wounds were photographed, excised, and fixed in 10% neutral-buffered formalin solution.

Wound Closure Analysis

Digital photographs captured on POD 9 were compared with initial photographs (POD 0) by two independent observers, who were blinded to the treatment mode, using planimetric methods (Scion Image, Scion Corporation, Frederick, Md.). Wound closure was quantified by measuring contraction, re-epithelialization, and open wound as a percentage of the original wound area. The sum of contracted, re-epithelialized, and open wound areas equals 100% of the original wound size [Sullivan et al. (2004) Plast. Reconstr. Surg. 113(3):953].

Microscopic Analysis

Wound biopsies were bisected, processed, and stained according to routine Hematoxylin and Eosin (H&E) protocols. Digital photographs were taken of the microscopic wound Sections at 40× magnification and panoramic cross-sectional composites of each wound were created using Adobe Photoshop® CS Software (Adobe Systems Incorporated, San Jose, Calif.). The digital images were analyzed with Scion Image™ software (Scion Corporation, Frederick, Md.) by two independent observers, blinded to experimental treatment mode, to quantify the area and thickness of granulation tissue. Capillary density was evaluated using 3 fields per slide viewed at 200× magnification: one in the middle of the lesion and one at each wound margin. The images were viewed with Adobe Photoshop® CS Software and blood vessels in each high-powered field were marked and counted.

Statistical Analysis

Values were expressed as means+/−standard deviation in the text and figures. One-way analysis of variance and ad hoc Dunnetts tests were used to determine the significance of differences between treatment modes.

Results

Wound Closure

Figure 6A:
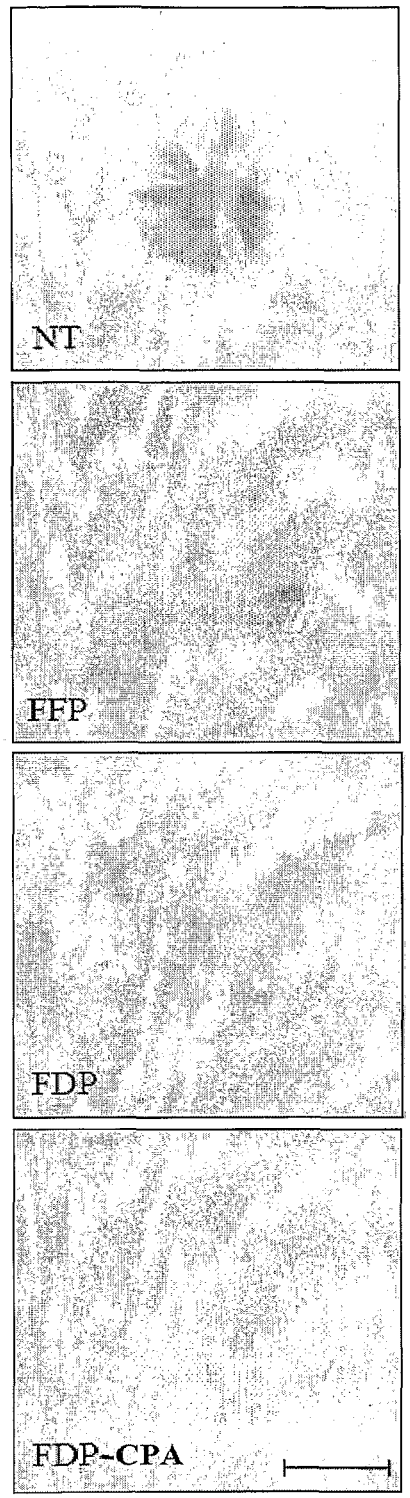
FIG. 6A is a series of photographs of diabetic mouse wounds after wounding that had not been treated (NT) or had been treated with fresh frozen platelets (FFP), platelets that had been freeze-dried and rehydrated in the absence of CPA (FDP), or platelets that had been freeze-dried and rehydrated in the presence of CPA (FDP-CPA). Scale bar, 500 mm.
Figure 6B:
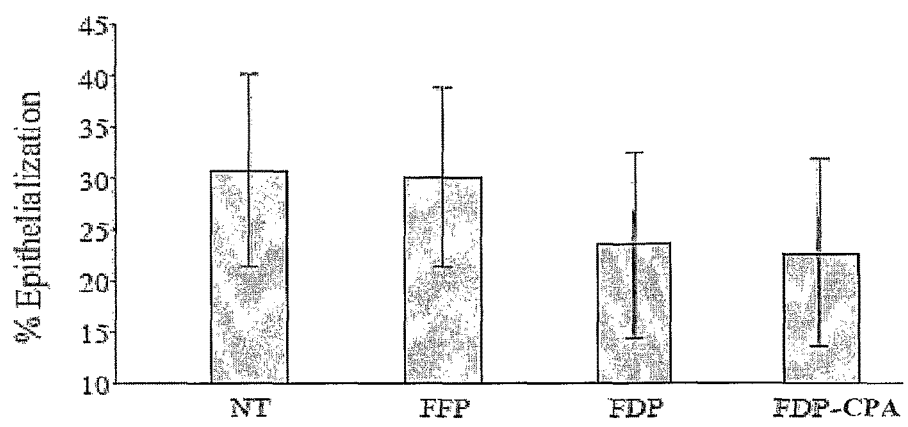
FIGS. 6B and 6C are bar graphs showing the percent (%) epithelialization (FIG. 6B) and percent (%) contraction (FIG. 6C) of the wounds shown in FIG. 6A. Scale bar, 5 mm.
Figure 6C:
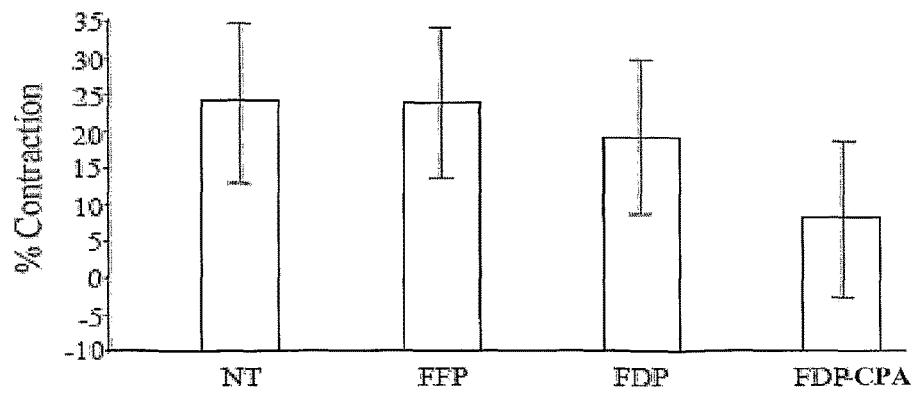

Wound healing occurred in all groups by a combination of wound contration and re-epithelialization. Previous work showed that a 1.0 square $cm^2$ wound in a diabetic mouse reaches the 50% closure point at about 8-12 days after surgery and that, once healed, there are no differences in either the histology or visual appearance of wounds in diabetic and control non-diabetic mice (data not shown). FIG. 6 shows that re-epithelialization was similar in all treatment groups but there was significantly reduced wound contraction in the FDP-CPA group compared to the other groups.

Granulation Tissue

Figure 7A:
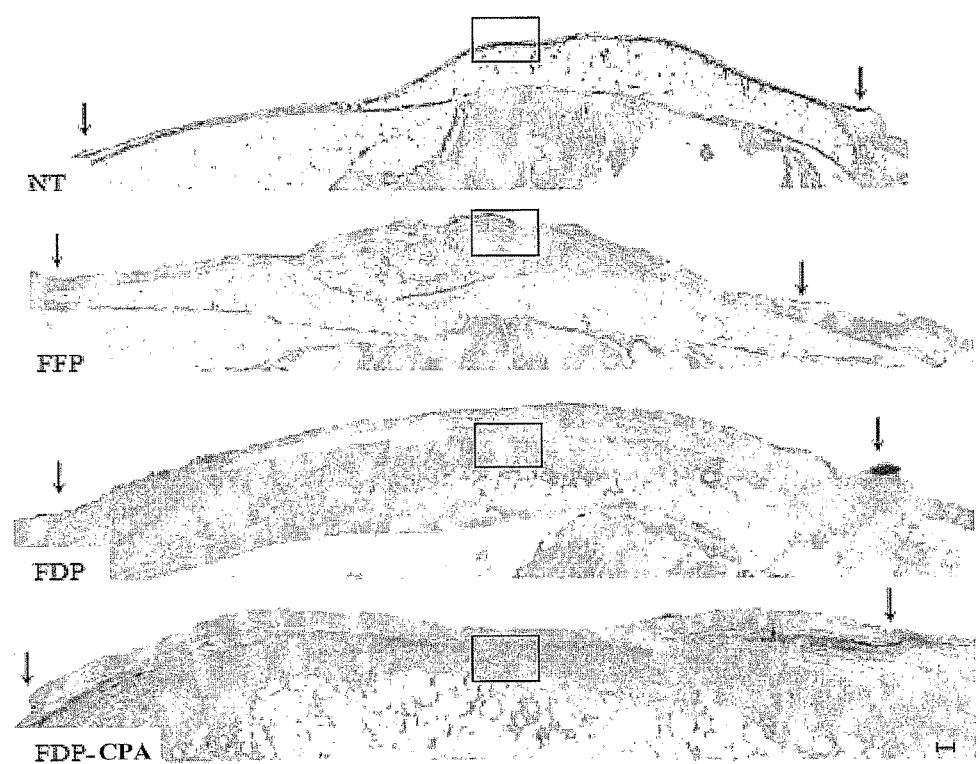
FIG. 7A is a series of photomicrographs showing the different amounts of granulation tissue deposition in histological Sections of the beds of the wounds shown in FIG. 6A. Arrows indicate epithelial margins and boxes indicate where measurements of tissue area and thickness were made (see FIGS. 7B and 7C). Scale bar, 100 μm.
Figure 7B:
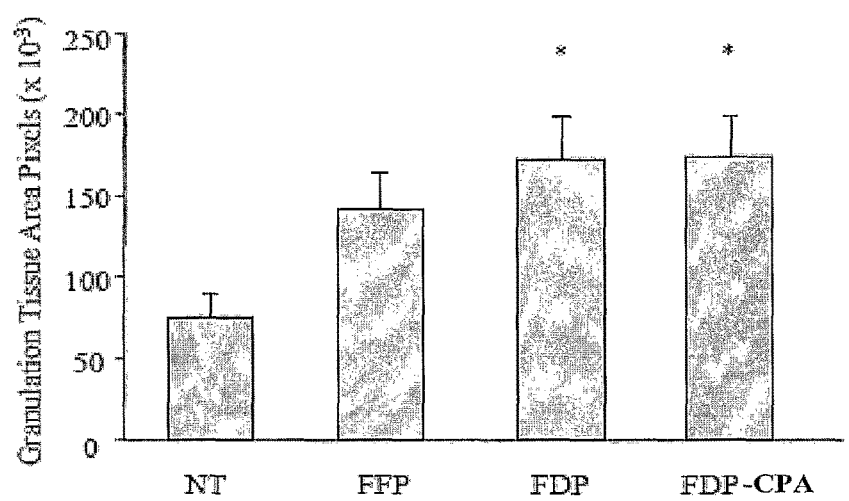
FIGS. 7B and 7C are bar graphs showing the granulation tissue area (FIG. 7B) and thickness (FIG. 7C) in the areas of the wounds shown by boxes in FIG. 7A. * indicates p<0.01.
Figure 7C:
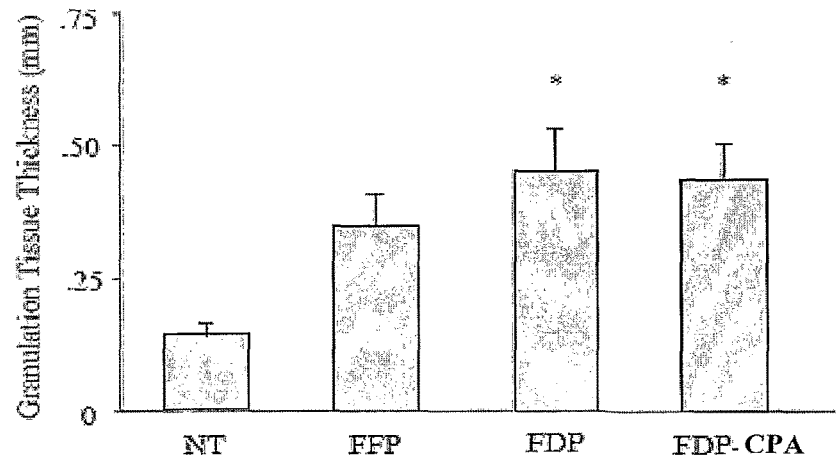

Panoramic cross-sectional digital images of each wound were prepared to analyze granulation tissue area and thickness (FIG. 7). Both FDP-CPA and FDP induced a significant ($p<0.01$) 2.3-fold increase in granulation tissue area compared with the NT group (FIG. 7). Treatment with FFP also stimulated the formation of granulation tissue when compared to untreated wounds ($p<0.05$), but it was visibly more edematous than either of the freeze-dried conditions. Similar results were observed with respect to granulation tissue thickness (FIG. 7). FDP-CPA and FDP treatments induced significant ($p<0.01$) 3.1 and 3.2-fold increases in granulation tissue thickness measured in the center of the wound, respectively, compared with the NT group. Tissue thickness in response to FFP treatment was also significantly elevated over NT ($p<0.01$) but failed to achieve comparable results to the freeze-dried treatment conditions.

Neovascularity

Increased tissue vascularity in response to treatment with platelet material was evident measuring standard H&E stained wound sections. FDP-CPA treatment resulted in significant ($p<0.01$) 2.2 and 1.8-fold increases in mean vessel count per high-power field compared with the NT group and the FFP group, respectively. FDP treatment induced a 1.6-fold increase compared with NT group ($p<0.01$).

What is claimed is:

1. A method of treating a cutaneous wound, comprising:
    administering to said cutaneous wound a dry platelet composition, wherein the dry platelet composition comprises a plurality of dry platelets; and inhibitors of platelet activation comprising at least one effector of the cyclic adenosine monophosphate (cAMP) second messenger system, at least one sodium channel inhibitor, and at least one effector of the cyclic guanosine 5' monophosphate (cGMP) second messenger system and wherein the dry platelet composition is applied to the cutaneous wound.

2. The method of claim 1, wherein the cutaneous wound is selected from the group consisting of a pressure ulcer, a venous stasis ulcer, a diabetic ulcer, an arterial ulcer, an injury wound, a burn wound, a complex soft tissue wound, a failed skin graft or flap, a radiation-induced wound, and a gangrenous wound.

3. The method of claim 1, wherein the inhibitors of platelet activation comprise adenosine, amiloride, and sodium nitroprusside.

4. The method of claim 3, further comprising hydrating the composition and after hydrating the composition a concentration of: about 10 µM to about 1 mM adenosine is obtained; about 0.1 mM to about 10 mM amiloride is obtained; and about 2.5 µM to about 250 µM sodium nitroprusside is obtained.

5. The method of claim 1, wherein the at least one effector of the cAMP second messenger system is selected from the group consisting of at least one of adenosine, 8-bromo cyclic adenosine monophosphate, or dibutyl cyclic adenosine monophosphate.

6. The method of claim 1, wherein the at least one sodium channel inhibitor is selected from the group consisting of amiloride analogues, bepridil, flecamide, saxitoxin, benzamil, and prajnalium.

7. The method of claim 1, wherein the at least one effector of the cGMP second messenger system is selected from the group consisting of L-arginine, nitrous oxide, SIN-1, SIN-1A, atrial natriuretic factor, vasopressin, oxytocin, and glyceril trinitrate.

8. The method of claim 1, wherein the composition comprises one or more cryoprotective agents.

9. The method of claim 8, wherein the cryoprotective agent is selected from the group consisting of dimethylsulfoxide, maltodextrin, dextran, hydroxyethyl starch, glucose, polyvinyl pyrrolidone, mannitol, and combinations thereof.

10. The method of claim 1, wherein the composition further comprises dry blood plasma.

11. The method of claim 1, further comprising hydrating the dry platelet composition in the cutaneous wound.

12. The method of claim 1, further comprising hydrating the dry platelet composition before application.

13. The method of claim 12, wherein hydration of the dry platelet composition results in a rehydrated platelet composition with substantially the same level of platelet function possessed by a sample of fresh platelets from which the dry platelet composition was obtained.

14. The method of claim 13, wherein the at least one platelet function is the ability to aggregate.

15. The method of claim 13, wherein the at least one platelet function is the ability to release one or more growth factors or chemokines.

16. The method of claim 15, wherein the growth factor or chemokine is selected from the group consisting of transforming growth factor-β (TGF-β), members of platelet derived growth factor (PDGF) family, epidermal growth factor (EGF), members of vascular endothelial growth factor (VEGF) family, and thymosin β4.

17. The method of claim 13, wherein the at least one platelet function is the ability to induce cell proliferation.

18. The method of claim 17, wherein the cell proliferation is fibroblast proliferation.

19. The method of claim 1, wherein the platelets are human platelets.

20. The method of claim 1, wherein the composition comprises a group of acellular tissue matrix particles.

21. A method of treating a cutaneous wound comprising:
administering to said cutaneous wound a dry platelet composition, wherein the dry platelet composition comprises a plurality of dry platelets; and inhibitors of platelet activation comprising adenosine, amiloride, and sodium nitroprusside and wherein the dry platelet composition is applied to the cutaneous wound.

22. A method of treating a cutaneous wound comprising:
administering to said cutaneous wound a dry platelet composition, wherein the dry platelet composition comprises a plurality of dry platelets; one or more cryoprotective agents; and inhibitors of platelet activation comprising at least one effector of the cyclic adenosine monophosphate (cAMP) second messenger system, at least one sodium channel inhibitor, and at least one effector of the cyclic guanosine 5' monophosphate (cGMP) second messenger system;
hydrating the dry platelet composition; and
applying the hydrated platelet composition to the cutaneous wound.

23. The method of claim 20, wherein the group of acelllar tissue matrix particles consists of acellular dermal matrix particles.

* * * * *